US010568726B2

(12) United States Patent
 Bringley (10) Patent No.: US 10,568,726 B2
(45) Date of Patent: Feb. 25, 2020

(54) PHOTOCOMPOSITE, LIGHT SOURCE AND THERMAL DETECTOR

(71) Applicant: Joseph F. Bringley, Rochester, NY (US)

(72) Inventor: Joseph F. Bringley, Rochester, NY (US)

(73) Assignee: TRANSPARENT MATERIALS, LLC, Rochester, NY (US)

( * ) Notice: Subject to any disclaimer, the term of this patent is extended or adjusted under 35 U.S.C. 154(b) by 0 days.

(21) Appl. No.: 15/228,651

(22) Filed: Aug. 4, 2016

(65) Prior Publication Data

US 2017/0035539 A1 Feb. 9, 2017

Related U.S. Application Data

(60) Provisional application No. 62/201,800, filed on Aug. 6, 2015.

(51) Int. Cl.
*A61C 13/15* (2006.01)
*A61C 1/00* (2006.01)

(52) U.S. Cl.
CPC .......... *A61C 19/004* (2013.01); *A61C 1/0015* (2013.01)

(58) Field of Classification Search
CPC .............................. A61C 19/003; A61C 19/004
See application file for complete search history.

(56) References Cited

U.S. PATENT DOCUMENTS

| 4,874,948 A * | 10/1989 | Cielo ..................... G01N 25/72 250/338.1 |
| 6,171,105 B1 * | 1/2001 | Sarmadi ............... A61C 19/004 433/29 |
| 7,066,733 B2 | 6/2006 | Logan et al. |
| 7,553,670 B2 * | 6/2009 | Rakow ................... G01N 25/72 436/34 |
| 8,568,140 B2 | 10/2013 | Kovac et al. |
| 9,066,777 B2 | 6/2015 | Gill et al. |
| 9,072,572 B2 | 7/2015 | Gill et al. |
| 9,211,695 B2 | 12/2015 | Paulson |
| 2002/0049389 A1 * | 4/2002 | Abreu .................. A61B 3/1241 600/558 |
| 2002/0133970 A1 * | 9/2002 | Gordon ................ A61C 19/004 34/250 |
| 2004/0058488 A1 * | 3/2004 | Arno ........................ G01J 3/32 438/200 |

(Continued)

FOREIGN PATENT DOCUMENTS

| JP | WO 2014050258 A1 * | 4/2014 | ........... A61C 19/004 |
| WO | WO 2011/140469 | 11/2011 | |

OTHER PUBLICATIONS

"Light-Curing Units: A Review of What We Need to Know", Price et al., Journ. Dental Res. (2015).

(Continued)

*Primary Examiner* — Sean M Michalski
*Assistant Examiner* — Shannel N Wright
(74) *Attorney, Agent, or Firm* — Lynne M. Blank, Esq.

(57) ABSTRACT

The invention provides a dental curing device comprising a light source having a wavelength capable of inducing polymerization of a photopolymer, and a noncontact thermal detector in alignment with said light source and capable of measuring the temperature or temperature change of the photopolymer upon polymerization.

18 Claims, 7 Drawing Sheets

(56) References Cited

U.S. PATENT DOCUMENTS

| | | | | |
|---|---|---|---|---|
| 2004/0122338 A1* | 6/2004 | Pompei | ............... | G01J 5/02 |
| | | | | 600/549 |
| 2005/0123877 A1* | 6/2005 | Duret | ............ | B29C 35/0805 |
| | | | | 433/29 |
| 2006/0044555 A1* | 3/2006 | Wang | ............ | A61C 1/0046 |
| | | | | 356/301 |
| 2006/0240376 A1* | 10/2006 | Plank | ............ | A61C 19/004 |
| | | | | 433/29 |
| 2009/0180118 A1* | 7/2009 | Feichtinger | ...... | F27B 17/025 |
| | | | | 356/402 |
| 2011/0228811 A1* | 9/2011 | Fraden | ............ | G01J 5/061 |
| | | | | 374/130 |
| 2011/0300505 A1* | 12/2011 | Jessop | ............ | A61C 19/004 |
| | | | | 433/29 |
| 2012/0026307 A1* | 2/2012 | Price | ............ | A61C 19/004 |
| | | | | 348/66 |
| 2012/0032575 A1* | 2/2012 | Noguchi | ........ | A61C 19/003 |
| | | | | 313/46 |
| 2014/0051040 A1* | 2/2014 | Kilcher | ............ | A61C 5/50 |
| | | | | 433/226 |
| 2014/0273240 A1* | 9/2014 | Georgeson | ...... | G01N 31/229 |
| | | | | 436/7 |
| 2016/0074144 A1* | 3/2016 | Peterson | ........ | A61C 19/004 |
| | | | | 433/29 |
| 2016/0113746 A1 | 4/2016 | Bringley | | |
| 2016/0282194 A1* | 9/2016 | Barnett | ............ | H01L 35/32 |
| 2017/0198093 A1* | 7/2017 | Crivello | ............ | C08G 65/22 |

OTHER PUBLICATIONS

"Light-curing of resin based composites in the LED era", Kramer et al., American Journ. Dentistry (2008).

\* cited by examiner

PHOTOCOMPOSITE, LIGHT SOURCE AND THERMAL DETECTOR

CROSS REFERENCE TO RELATED APPLICATIONS

Priority is claimed and reference is made to commonly assigned, U.S. Prov. Patent Application: Ser. No. 62/201,800 by Bringley et al., filed Aug. 6, 2015 entitled "PHOTOCOMPOSITE, LIGHT SOURCE AND THERMAL DETECTOR", the disclosures of which are incorporated herein by reference.

FIELD OF THE INVENTION

The present invention relates to photopolymerizable composites and coatings and an associated light polymerization device. The composite or coating comprises a least one photopolymerizable resin, and optionally inorganic fillers and a photoinitiator. The light polymerization device comprises a light source and a thermal detector. The device is able to monitor the photopolymerization process and to indicate that polymerization is complete. The invention relates to any photopolymerizable composite or coating including industrial, printing, microelectronic, protective, biomedical and dental composites and coatings.

BACKGROUND OF THE INVENTION

Inorganic-organic polymer composite materials are used in a wide variety of applications including structural materials, high performance composites, optical components, aerospace, biomedical implants and dental applications. Generally, composites are employed where performance requirements are demanding and not easily fulfilled with traditional structural materials. For example, inorganic materials such as glass, ceramic and stone are very hard, scratch resistant and even sometimes transparent (e.g., glass) but suffer from the fact that they are very heavy and brittle. Polymers, conversely, are light and durable but have poor hardness, abrasion and wear resistance. Composites, made from the combination of inorganic materials and polymers, may have properties that lie in between, potentially providing materials that are simultaneously strong but lightweight, hard but flexible, abrasion resistant and durable.

In order to achieve such properties, in practice, hard inorganic materials are mixed into polymers, or polymer precursors, monomers and/or oligomers, (hereafter collectively referred to as resins) and the mixture is then cured to form a composite. In recent years, the polymer industry is transforming from composites that are polymerized, or "cured", using heat (thermal set polymers) to composites that are cured using ultraviolet or visible light, or low energy electrons (hereafter called UVEB resins). UVEB curable resins offer tremendous energy and waste savings to the coatings and composites industries because they are polymerized (cured) directly with light or low energy electrons, and also because they generally do not contain volatile diluents such as solvents or carriers that may be considered hazardous air pollutants. UVEB curing is far more energy efficient since it overcomes the thermal loss that is prevalent in conventional thermoset coating systems. Ironically, the fundamental advantages of UVEB systems, where a solventless medium is cured rapidly by radiation, are also the source of significant system limitations.

Light curing requires that the coating and/or object must be sufficiently transparent in the spectral region of curing, since the penetration depth and absorption of the curing radiation is essential to achieve rapid and efficient curing. This limits the performance additives (fillers, stabilizers, functional additives, and coating aids) that can be added to UVEB systems since the additives must also fulfill the requirement of being sufficiently transparent in the curing region of the spectrum. Furthermore, in thick coatings or composites, the degree of curing may vary across the specimen due to the attenuation and absorption of curing radiation. To overcome this problem, in practice, it is common to "overexpose" the specimen with curing radiation in order to assure that curing is complete or near complete. This is not ideal since energy and time are thereby wasted. Furthermore, in medical applications such as dentistry, overexposure may increase risk to the patient.

The dental industry, primarily due to health concerns, is rapidly transitioning dental restoratives (e.g., cavity fillings, dental restorations, adhesives, etc.) from the conventional mercury based amalgams to highly filled, light curable, resin based composites. Resin based composites are safer and better match the color and appearance of human tooth enamel, but are often softer, not as strong or as durable as the traditional metal amalgams. To resolve these problems, manufacturers have developed microfilled polymer composites that have strength, hardness and durability close to that of the conventional amalgams. Typically the resin based composite paste is applied or packed into a tooth cavity and then cured using a hand-held light wand. The light wand is held in proximity of the composite for a period of time believed necessary to fully cure the paste with the intention to create a hard, strong and durable composite.

There is a significant clinical problem, however, in that inadequate curing can lead to premature failure of the composite requiring clinical revision of the restoration and significant patient cost. The extent and significance of the problem has been described in recent dental publications including "Light-Curing Units: A Review of What We Need to Know", Price et al., *Journ. Dental Res.* (2015), and "Light-curing of resin based composites in the LED era", Kramer et al., *American Journ. Dentistry* (2008), and are incorporated herein by reference. The cure rate and cure depth of a restoration is dependent upon a number of factors including the composite thickness, composite color, light absorption and attenuation of light within the composite. This is further compounded by the variability in lamp designs and power outputs of lamps from various manufacturers, and the degradation of the lamp over time, and yet even further complicated by user variability in terms of how far the lamp tip is held from the composite and for how long the composite is irradiated with polymerizing light. Today, a dentist may follow manufacturer's guidelines, but still has no method of determining if the restoration was sufficiently cured.

PCT WO 2011/140469 to Fathi et al., discloses a polymerizable composition including at least one monomer, a photoinitiator capable of initiating polymerization of the monomer when exposed to light, and a phosphor capable of producing light when exposed to radiation (typically X-rays). The material is particularly suitable for bonding components at ambient temperature in situations where the bond joint is not accessible to an external light source. There is a problem, however, in that the invention is directed toward curing (with X-rays) opaque structures that are not accessible to UV or visible light. There is an additional problem in that the invention does not include a detector system capable of indicating that polymerization is substantially complete.

U.S. Pat. No. 9,211,695 B2 to Paulson is directed toward monitoring the polymerization of photopolymerizable inks and discloses a monitoring device including a light source, an optical filter, and an optical detector. The monitoring device may monitor curing processes, such as ultraviolet (UV) curing processes to determine the progression of the level of cure of a light-activated material to a substrate. The infrared light source emits light toward a light-activated material, such as a film, and/or a substrate. The optical filter is positioned so that a wavelength of the light is transmitted through the optical filter after the light is reflected off of the substrate and/or the film. The optical detector is positioned to detect the light that is transmitted through the optical filter. There is a problem however in that this method is directed toward measuring the change in reflectance of a photopolymerizable target after it has been polymerized, it requires multiple light sources and is optically complex, and further the method is not demonstrated by working examples in the patent.

U.S. Pat. No. 7,553,670 B2 to Rakow et al. discloses a method of monitoring a polymerization in a three dimensional sample comprising an initiation surface and a separate one or more monitoring surfaces, said monitoring surfaces substantially perpendicular to said initiation surface, wherein the method comprises initiating said polymerization at or on said initiation surface, and capturing a thermographic profile at a plurality of points on at least one monitoring surface of said sample with an infrared detector array. There is a problem however in that the method requires a perpendicular geometry, it requires bulky infrared cameras, and cannot be easily adapted to a hand-held device. There is a further problem in that the method does not provide for automation of the device.

Problem to be Solved

The inventors have recognized that there is a problem in that there is, currently, a lack of useful methods of indicating the degree of polymerization within a composite in real-time and that both under cured and overexposed composites may directly result. Under cured composites may lack strength and suffer with respect to mechanical properties, whereas overexposure wastes time and energy. There is a need for a device and/or a device system that may indicate whether the proper exposure of curing radiation has been applied to the composite or coating. There is further a clinical need in the dental industry for hand-held curing systems, that may indicate in real-time the proper light exposure for the curing of dental restorations.

SUMMARY OF THE INVENTION

The invention provides a dental curing device comprising a light source having a wavelength capable of inducing polymerization of a photopolymer, and a noncontact thermal detector in alignment with said light source and capable of measuring the temperature or temperature change of the photopolymer upon polymerization.

Advantageous Effect of the Invention

The invention provides a simple and reliable device that may indicate, in real-time, information regarding the degree of polymerization of a composite or coating. The information can be used to determine the degree of cure and/or determine if the cure has been complete. The invention may improve substantially the efficiency of photopolymerization processes. In dentistry, the invention provides for better quality teeth restorations that have improved durability, leading to better patient outcomes.

DETAILED DESCRIPTION OF THE INVENTION

The invention is directed toward photocurable composites and coatings and an associated light curing, or polymerization, device. The composite or coating comprises a least one photopolymerizable resin, and, optionally, inorganic fillers and a photoinitator. The light curing device comprises a light source capable of initiating polymerization, and a thermal detector capable of detecting a temperature change within the object. Preferably, the light source and thermal detector are coupled via a feedback loop. The device monitors the composite and/or coating as it is being photocured, and, by means of an algorithm, indicates the degree of polymerization, or that polymerization is complete. The invention relates to any photopolymerizable composite or coating including industrial, printing, microelectronic, protective, biomedical and dental composites and coatings.

Terms and Definitions

A photopolymer is any monomer, group of monomers, oligomer, pre-polymer or polymer capable of being polymerized or cured by electromagnetic radiation having a wavelength of less than about 2000 microns.

"Polymerized" and "cured" are used herein interchangeably and mean the same; photopolymerized and photocured also mean the same.

Photopolymerization or photopolymerizable, photocurable and light curable as used herein, refers to a process, or materials, in which monomers, oligomers or pre-polymers (hereafter collectively referred to as resins) are polymerized or cured using electromagnetic radiation, such as X-rays, electron beams, and ultraviolet and actinic light.

A thermal detector as used herein, refers to any device capable of measuring a temperature or a temperature change.

A noncontact thermometer as used herein, refers to any device capable of measuring a temperature or temperature change of an object without coming into physical contact with the object.

"In alignment" with said light source, as used herein, means that the noncontact thermal detector and light source are focused upon substantially the same position, or the same spot of a target object.

The invention provides a device comprising a light source having a wavelength capable of inducing polymerization of a photopolymer, and at least one thermal detector capable of measuring the temperature or temperature change upon polymerization of the photopolymer, wherein the temperature or temperature change is used to indicate the approximate degree of polymerization. As shall be demonstrated in the inventive examples contained herein, the device can predict the "cure state" or degree of polymerization of the photopolymer in real-time. The device may also be tailored to predict the degree of polymerization for endothermic processes, by measuring the negative temperature changes. It should be noted, that the degree of polymerization (meaning the degree of conversion of monomers or oligomers) may not be 100% for a "fully cured" specimen. This is because some monomers may be physically trapped and prevented from polymerization by steric forces, and/or side reactions, or inefficiencies inherent to the polymerization process. Typically, cured photopolymers have a conversion rate that is about 50-90% conversion of monomer species. Because the chemical reaction of polymerization is typically an exothermic process and generates heat, the heat generated may be used to characterize the process in considerable detail, and as shall be demonstrated, can be used to adequately predict specimen cure.

The device comprises a light source, also referred to as a curing radiation source, having a wavelength capable of inducing polymerization of a photopolymer. The wavelength of the emitted light may be any wavelength capable of inducing polymerization in the target specimen, however it is preferred that the light source is an X-ray, electron beam, ultraviolet or visible light source. It is most preferred that the light source is a visible light source. This is preferred because visible light sources are safer for both the operator and, in the case of medical devices (including dental devices), the patient. It is still further preferred that the light has a wavelength between about 365-550 nm. In the application of the invention in the coatings industry, it is preferred that the curing radiation is from an ultraviolet source. In the medical or dental industry, it is preferred that the curing lamp is a long wave ultraviolet or blue light emitting source. It is most preferred for dental applications, that the lamp is a blue emitting LED source, as such lamps have excellent power stability and are safer for the patient.

A variety of dental curing lamps are available commercially including quartz tungsten halogen lamps, plasma arc lamps, argon ion lasers and light emitting diode (LED) lamps (both single wave and polywave LED, pulsed or continuous). The invention described herein may be configured to work with any of these lamps.

High power LED elements are one suitable type of elements for the inventive device. For example, a high power dental LED might be used. The light emitting engine might use a single LED element or a plurality of elements in an array. The LEDs may be arranged in a pattern, such as a circular pattern.

The radiation from the light source, such as an LED array, may be captured by a light transmitting device, such as an optical fiber light pipe, and transmitted and directed through the light pipe and onto the working surface, such as a tooth surface. The light pipe would preferably be a conventional light pipe formed by fusing together a plurality of optical fibers. One embodiment of such a light pipe maintains a uniform diameter along its length. In another embodiment, a focusing light pipe might be utilized, which gathers the light from the LED array at one end, and transmits the radiation at a smaller or tapered end to further define, and concentrate the curing light beam for use on a smaller work surface. The light source, particularly LED dies, and light pipe are positioned within a suitably shaped housing. Alternatively, the light source, for example, an array of small dies, may be positioned on the tip of the curing device to directly irradiate the dental compound instead of using a light pipe. A surface mounted light source can utilize a separate lens for focusing the irradiated light.

The light pipe can be bent or curved for directing the light beam in a downward direction onto the work surface, such as a tooth surface. The light pipe is also rotatable. The tip itself can be bent curved or rotated to direct the beam in other directions.

The curing device may include at least one lens. The lens can be located over the LEDs or other light emitting structures in order to focus the light distal end of the tip, and ultimately the distal end of the curing light device. In use, the distal end is positioned proximate to a work site, such as a site containing dental composite material that is to be cured. Light generated from the light source is captured and collimated and effectively reflected in the body of the lens element to be directed out of the distal end. In one embodiment of the invention, the lens element is a total internal reflector (TIR) lens element that is configured for capturing, collimating, and efficiently directing the light out to the end of the lens element for less optical loss and greater delivery of light energy to the curing site. The lens may be a converging or diverging optical lens. Various reflectors can be used with the lenses. Additional components, such as a clear protective coating or windows can be applied over the light source.

One skilled in the art may select the appropriate photoinitiator, and other addenda, for use in the photocurable composite after consideration of the emittance wavelength and emittance power of the lamp.

The device comprises at least one thermal detector that can measure and record the temperature of the specimen during the time that it is exposed to the light source. In principle, the thermal detector can be a thermometer and may be any thermometer capable of measuring temperature. However, in practice of invention, digital or analog devices that can record the temperature at high acquisition rates are preferred. Examples of suitable thermometers include thermocouples. In principle, only one thermocouple is needed, however, it is possible to use multiple thermocouples to record the temperature at various positions within the specimen. This is especially useful for three dimensional objects that are cured using X-ray or electron beam radiation.

It is most preferred that the thermometer is a noncontact thermometer. Noncontact thermometers are able to measure the temperature of an object with out coming into contact with the object. Examples of noncontact thermometers suitable for practice of the invention are infrared thermometers, optical pyrometers, thermopiles and thermal imaging cameras. For applications where the specimen size is very small (less than about 1-2 cm diameter) a thermopile, or focused thermal imaging camera is preferred.

In one embodiment, the noncontact thermal detector is a thermopile sensor, since thermopile sensors may be fabricated at sizes as small as about 200 microns and therefore can be housed within the lamp tip. If the lamp is a blue light LED dental lamp, it is preferred that the thermopiles be housed within the same printed circuit board as the blue emitting LED's.

In the present invention, the thermal detector itself is placed so as to not be in the path of the light emitted by the light source. However, the light source and thermal detector are aligned so that the area detected by the thermal detector is located within the area illuminated by the light source.

The device may also contain at least one reference thermal detector used to detect heat not associated with the area illuminated by the light source. The reference thermometer can be aligned with the light source in any position, provided it does not "see" the illuminated curing area.

In its most simple form, the invention comprises a light source and a noncontact thermal detector placed adjacent to the tip of a light curing device. The most preferred device is hand-held and may be self-contained or a housing and a tip structure, which may be removably coupled. The device also may include suitable control electronics. Some control electronics may be coupled with external controls that may include buttons, switches, or other suitable manual controls for controlling the device. A display device might also be utilized and may include a screen, individual light elements, or other graphical elements for providing a visual display of the operation of the device. In one embodiment, the tip structure of the device includes a proximal end, opposite the distal end, that is removably coupled with the housing. The distal end, with the light source and thermal detector, is placed within the mouth of a patient for curing a light curable compound. The device is also connected to a power supply.

The tip portion is appropriately formed and may include an angled distal or radiating end to direct a curing light beam out of the housing and onto a tooth surface or other work surface. The shape of the tip and housing may vary. They might be vented for heat dissipation purposes. The power supply might be positioned in line with the tip to reduce or eliminate any handle portion to streamline the design, such as for a small, pocket curing light.

The system can record the temperature or temperature change produced by the amount of energy an operator actually delivers to the photopolymerizable resin restoration in the mouth. The information can be recorded and displayed in real-time and can be used to optimize the exposure time based on a predetermined temperature or temperature change.

When the light source comprises multiple sources, such as multiple LEDs, the light emitted from each LED has an axis of emission. It is preferred that the axis intersects the curing surface at angles of from 30 to 150 degrees, preferably 70 to 110 degrees, and most preferably 80 to 100 degrees. The multiple sources may produce a plurality of divergent radiation paths, that is, all of the LEDs are not directed to a single common focal point.

The noncontact thermal detector is placed adjacent, or as close as possible to, the lamp tip or to the exit of the curing light. In a preferred case the noncontact thermal detector is a thermopile(s) and is placed directly adjacent to the lamp tip or exit of the curing light. This is preferred because the thermopile has its greatest sensitivity when it is oriented perpendicular, or normal, to the target surface, and further the lamp has its greatest irradiance at an angle perpendicular, or normal, to the surface of the target. Thus, in the preferred embodiment, the thermopile and the light source are "aligned." In a most preferred case, the thermopile(s) are fabricated or mounted directly on the circuitry (such as a printed circuit board) that contain the LEDs, and all the devices are substantially coplanar.

It is preferred that the light is collected and detected as close to the tip or light exit position of the lamp as possible since this allows for correcting the cure time based upon the position of the lamp tip or light exit position. For example, if the lamp tip and detector are moved closer, both cure irradiance and emission irradiance increase and the device can properly predict that the curing period is shorter. Likewise, if the lamp is held at a distant position, then both decrease and the device can predict that the curing must continue for a longer time. The light may be collected at the tip or light exit position by placing the detector at this position, or alternatively by placing one or more fiber optic cables or bundles at this position to collect the light, and to provide a conduit so that the light may reach the detector.

The noncontact thermal detector is placed in alignment with the axis of emission of the curing lamp. By "alignment" it is meant that the noncontact thermal detector is focused to a spot directly within the beam of the light source as it impinges upon the target. It is preferred that the noncontact thermal detector is focused substantially within the center of the column or beam of curing light. This is preferred because temperature measurement outside of the beam of curing light may cause noise or unwanted thermal signal. It is preferred that the noncontact thermal detector is focused to a spot size that is less than the diameter of the curing light beam, and most preferably less than about half the diameter of the curing light beam.

Focusing of the noncontact thermal detector can be accomplished by means of a lens. The optical design of the lens determines the "field of view" and at a particular distance, the "spot size" of the detector. The spot size of a noncontact thermal detector refers to the area over which it measures the average temperature. See FIG. 1, 28. The spot size increases as the detector is moved away from the target, and for a given distance can be computed from the devices "field of view", which is typically given as a specification by the manufacturer. The larger the field of view, the greater the spot size. It is preferred that the thermopile sensor has a field of view of less than 90 degrees, and more preferably less than 30 degrees. It is preferred that the device is focused to a spot size of less than about 1 cm, and more preferably to a spot size of less than 3 mm, and even more preferably to a spot size of less than 1.5 mm. This is preferred because it is important that the device is focused on the polymerizing composite and not onto adjacent tooth structure, especially in the case of a very small dental restoration.

Figure 7A:
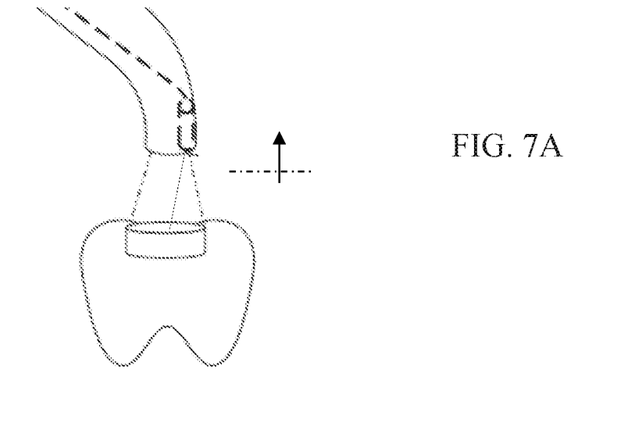
FIG. 7A is an enlargement of the section of FIG. 2 illustrating the side view of the light source showing the perspective axis of FIG. 7B.
Figure 7B:
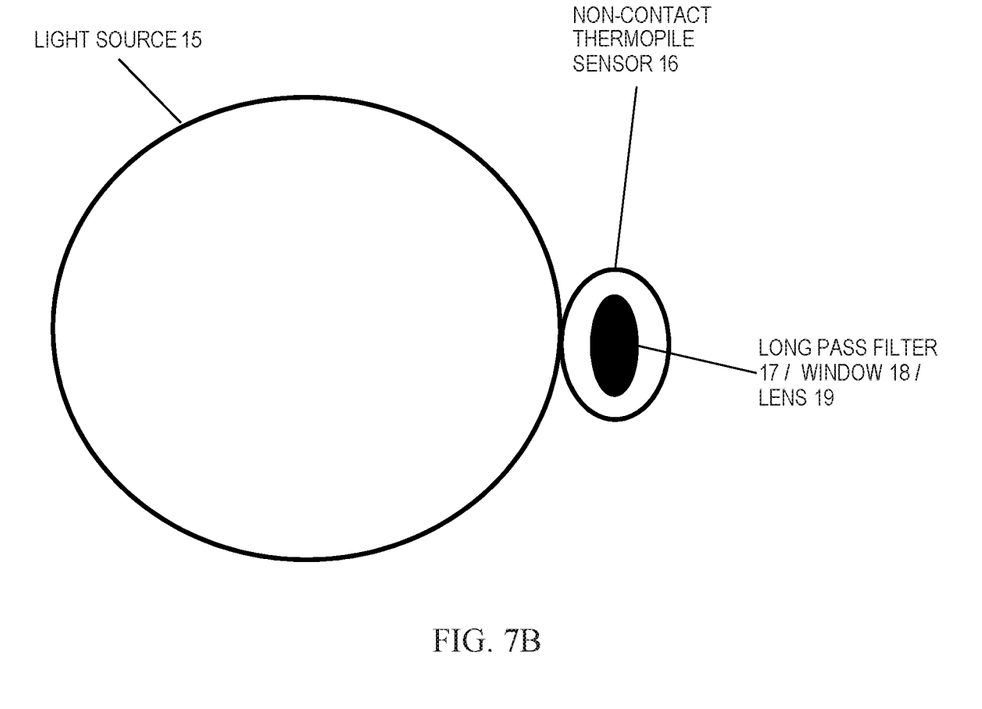
FIG. 7B is an illustration of a hand-held medical or dental device for curing tooth restorations or biocomposites from a perspective view looking into the light source.

It is preferred that the thermal detector, especially a thermopile sensor 16, is shielded from the blue LED curing lamp by means of a long pass filter 17 (FIG. 7B) having a cut-off wavelength greater than 1000 microns. This is preferred because the intense blue light may interfere with the operation of the thermopile sensor. Long pass filters suitable for practice of the invention include germanium and silicon windows 18, germanium windows are most preferred. The light shield in some cases may serve a dual function both as a lens 19 and a light shield.

In a particular embodiment, the light source and the thermal detector are connected via a feedback loop such that the detector indicates that the composite has absorbed sufficient incident radiation to cure the composite. To create such a feedback loop, electronic hardware is employed to record the temperature or temperature change output versus time, and software is employed to examine the data and to predict cure. The device system of the invention can be designed and programmed to examine real-time data to recognize steady state temperature or temperature change. After the steady state is detected the device may simply indicate to the user, by any visual or audio means, that cure is complete. Alternatively, the device may simply turn itself off, i.e., turn the light source off.

The system can include an analog/digital converter for converting analog signals from the detector to digital signals for further processing by the processor and a custom power meter. The output from the processor can be provided via Bluetooth, USB ports, a system bus, or direct connection to a computer or a PDA or any other suitable display (audio, visual, or mechanical). The energy received by the simulated dental restoration in real-time and via an intra oral video of the procedure can be displayed to the operator.

The electronic signals received from the processor are processed at the direction of software instructions that are stored, for example in nonvolatile memory, and loaded into RAM.

The software can further instruct the processor to store, in a database, a user profile including an ability of a user to deliver the predetermined amount of energy to the simulated dental restoration. The software can also provide suitable user interfaces for conveying the real-time measurements to a user in various forms.

The light curing device is connected to a power supply, either directly or through a housing or a base. The power supply can be a suitable external power supply, such as an AC or DC source. The device can use a connection via power cord or in the form of rechargeable internal or external elements. The device might also be configured to fit within a suitable structure, such as a standalone, table-mounted base, a mounting structure for mounting it on a wall, pole, or chair, or might be incorporated in a portion of a dental chair for holding and charging the curing device.

The supplied power may then be controlled via suitable control circuits, such as to control the intensity of the light emitting device, the duration of its illumination, and various other parameters associated with the operational modes of device. The device contains suitable control circuitry and a power supply circuit, along with the various electrical connections/circuits for powering the tip structure and the light emitting device at its distal end. In one embodiment of the invention, the power supply circuit includes rechargeable supply elements, such as a battery, which may be charged and removed from the external power source to be manipulated by an operator. An ultracapacitor element or circuit might also be utilized to provide the desired power for the light emitting device.

In many cases, the light source generates some heat, and therefore, is mounted on a simple heat sink, which may be utilized with or without a forced air device, such as a fan, to further dissipate the heat. The tip structure can include a heat sink structure or element that extends in the tip structure from the proximal end to the distal end. In another embodiment, the heat sink can extend past the proximal end of the tip structure to engage the housing for appropriate thermal transfer of heat from a curing light device. The heat sink may be made from a suitable heat-transfer or heat-conducting material, such as a metal (e.g. copper) or aluminum. In particular cases, it may be necessary to shield the noncontact thermal detector from heat generated by the lamp by means of a heat sink.

The curing device can contain other elements. In some embodiments, an intra-oral camera can be provided. The camera can record video or still images of the curing energy source as an operator is manipulating it during a restoration. The camera can further be connected to the processor, which can process the video or images.

It is preferred that the device includes an audio signal indicating that polymerization is complete, and the light source is powered off at the indicating signal. This is preferred because it indicates to the operator that they have applied light energy sufficient to cure the composite filling.

The light curable resin may be selected from any photopolymerizable molecule, monomer, oligomer, or prepolymer (hereafter light curable resins). Particularly preferred light curable resins suitable for use in the application of the invention include hardenable organic materials having sufficient strength, hydrolytic stability, and nontoxicity to render them suitable for use in the oral or in vivo environment. Examples of such materials include acrylates, methacrylates, urethanes, carbamoylisocyanurates, epoxides, and mixtures and derivatives thereof. One class of preferred hardenable materials includes materials having polymerizable components with free radically active functional groups. Examples of such materials include monomers having one or more ethylenically unsaturated group, oligomers having one or more ethylenically unsaturated group, polymers having one or more ethylenically unsaturated group, and combinations thereof. In the class of hardenable matrix resins having free radically active functional groups, suitable light curable components for use in the invention contain at least one ethylenically unsaturated bond, and are capable of undergoing addition polymerization. Such free radically ethylenically unsaturated compounds include, for example, mono-, di- or poly-(meth)acrylates (i.e., acrylates and methacrylates), such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycoldimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth) acrylate, sorbitol hexacrylate, tetrahydrofurfuryl (meth) acrylate, bis[1-(2-acryloxy)]-p-ethoxyphenyldimethylmethane, bis[1-(3-acryloxy-2-hydroxy)]propoxyphenyldimethylmethane, ethoxylated bisphenol A di(meth)acrylate, and trishydroxyethyl-isocyanurate trimethacrylate; (meth)acrylamides (i.e., acrylamides and methacrylamides), such as (meth)acrylamide, methylene bis-(meth)acrylamide, and diacetone (meth)acrylamide; urethane (meth)acrylates and the bis-(meth)acrylates of polyethylene glycols. Other suitable free radically polymerizable compounds include siloxane-functional (meth)acrylates and fluoropolymer functional (meth)acrylates. Mixtures of two or more free radically polymerizable compounds can be used, if desired. Other matrix materials or polymers may also be incorporated. Examples of other useful matrix polymers include natural and synthetic biopolymers, such as peptides, proteins, gelatin, poly(lactic acid), poly(glycolic acid), poly(caprolactone), chitosan and its derivatives, alginates, starches and the like.

The composites of the invention typically contain a photoinitiator that is capable to absorb the incident (curing) radiation of a first wavelength and to initiate the polymerization/curing reaction. The photoinitiator may optionally be combined with a sensitizer or accelerator. The choice of photoinitiator may be dependent upon the wavelength of the curing radiation. For X-ray or electron beam radiation, a photoinitiator is not typically required since these high energy wavelengths may directly initiate polymerization. For ultraviolet curing, the photoinitiator is typically selected so that it absorbs energy between about 180-450 nm. For blue light curing, the photoinitiator is typically selected so that it absorbs energy between about 400-500 nm. Examples of suitable UV and visible photoinitiators are those sold under the trade name Irgacure® and Lucirin® (BASF Corp. Charlotte, N.C.) or under the trade name Darucor® (Ciba Specialty Chemicals). It is preferred that the photoinitiator is a blue light photoinitiator that is photobleachable. For dental or medical applications, it is preferred that the photoinitiator is camphorquinone or TPO (2,4,6-trimethylbenzoyldiphenylphosphine oxide). It is further preferred that the camphorquinone is used together with a polymerization accelerator such as an amine, or any other molecule capable of accelerating the reaction. An example of a suitable accelerator for practice of the invention is ethyl-4-N,N-dimethylamino benzoate.

The light curable coatings or composites of the invention may contain addenda such as flow agents, thickening agents, coating agents, surfactants and performance agents that improve the manufacturability of the article, or improve the physical properties of the final composite or coating. In the coating industry, it is common to add performance addenda that improve adhesion, scratch resistance, hardness and durability of the article. It is preferred that such addenda do not substantially absorb the curing radiation, since the absorbance by addenda may adversely affect the polymerization rate.

There are several methods known within the industry to counteract the absorption of curing radiation by addenda. The first is to include nanoparticles within the coating or composite formulation. Because of their small size (less than about 100 nm), nanoparticles often may not absorb or scatter the curing radiation and hence may be transparent to both the curing, emitted and visible wavelengths. A second method to control this problem is to match the refractive indices of the uncured resin and performance addenda materials. If the addenda have the same, or nearly the same, refractive index as the resin then the curing radiation is not significantly scattered by the performance addenda. This is especially important in the dental industry where the filler loadings are remarkably high (typically about 80 weight percent in order to obtain hardness comparable to teeth). Further the refractive index is matched to provide a composite (tooth restoration) that is aesthetically appealing, attempting to recreate the optical translucency and visual brilliance of natural teeth. It is preferred that the refractive index difference between the resin and fillers is not greater than 0.05, and more preferably not greater than 0.025.

A wide variety of dental filler materials are available to aid formulators in achieving such properties. The filler materials, useful for the purpose of practicing the instant invention include silica-alumina, silica-titania, silica-zirconia, and silica rare-earth mixed oxides as described in H. Suzuki et al. "Refractive index adjustable fillers for visible light cured dental resin composites: preparation of $TiO_2$—$SiO_2$ glass powder by the sol gel process." *J. Dental Research*. 883 (1991) and in U.S. Pat. Nos. 4,217,264, 4,503,169, 4,764,497, 5,856,374, 6,572,693, 6,730,156 and 8,617,306, all incorporated herein by reference in their entirety. Also useful for practice of the invention are refractive index controlled glasses, sometimes referred to as dental glasses, and exemplified most typically by barium glass or strontium glasses, available form Schott Corp. Still other useful materials are nanoparticles or nanoparticle dispersions as described in U.S. Pat. Nos. 5,609,675, 6,060,830, 6,572,693, 6,899,948 and Japanese Patent Kokai JP07-291817, all incorporated herein by reference in their entirety. Still other useful materials are fumed, colloidal or precipitated silicas, aluminas, and radiopaque materials such as zirconia, nano-zirconia, ytterbium fluoride and yttrium fluoride.

Composites may often contain more than one performance addenda (fillers), over even combinations of many fillers. In this case the primary filler is the filler that is used in the greatest quantity. It is preferred that both the resin and the primary filler have a refractive index between about 1.44 to 1.55, and more preferably about 1.49 to 1.54.

Figure 1:
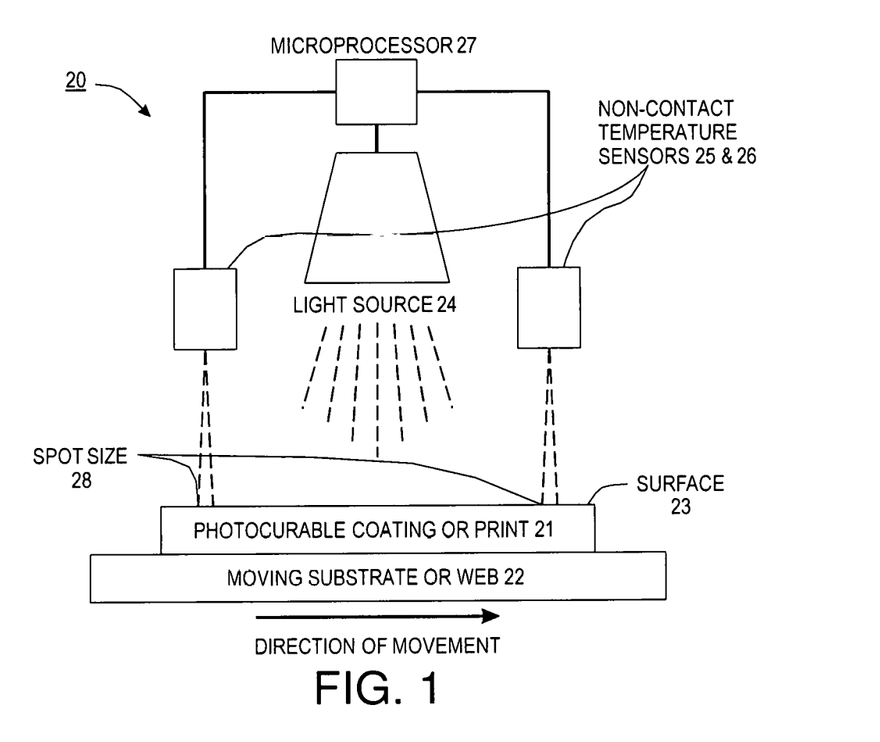
FIG. 1 is an illustration of the device for use in coating operations where typically a moving substrate contains a photopolymer film, or photopolymer inks that are cured.
Figure 2:
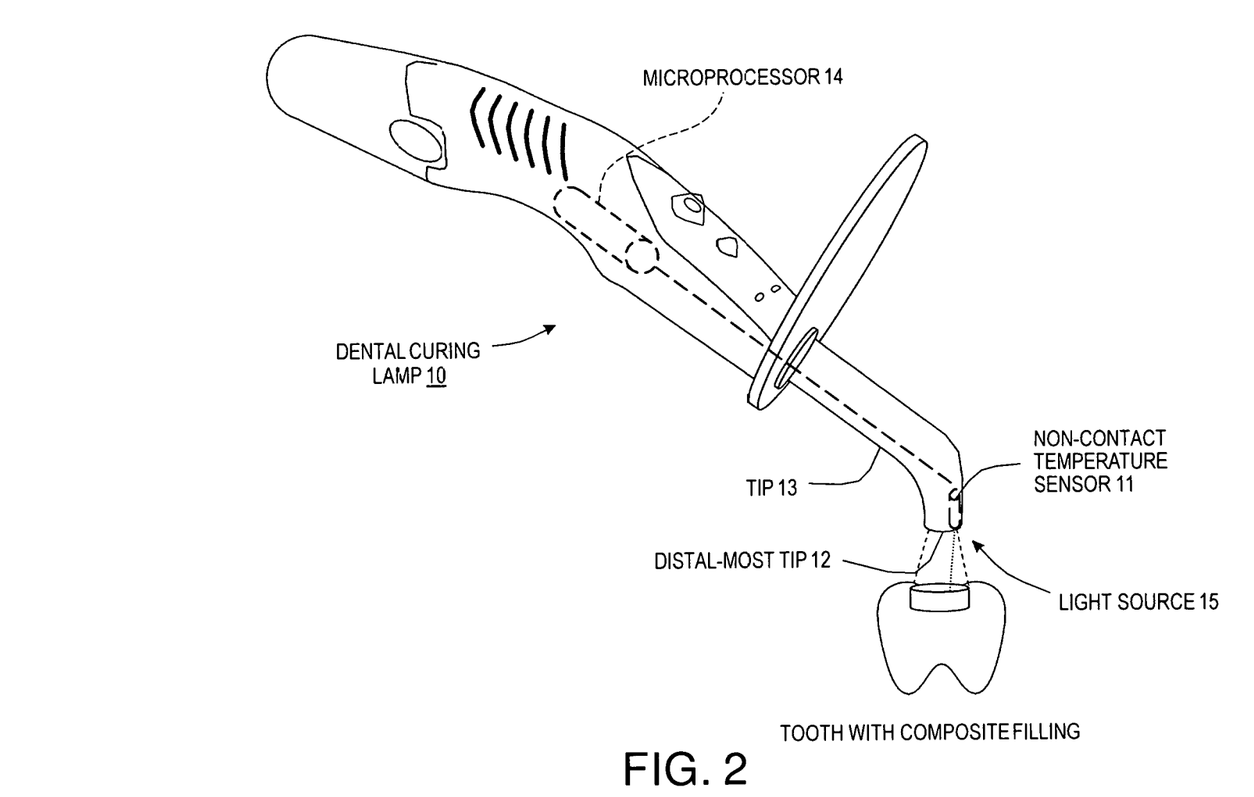
FIG. 2 is an illustration of a hand-held medical or dental device for curing tooth restorations or biocomposites.

The practical application of the invention can be understood by reference to FIG. 1-2. FIG. 1 shows a specific embodiment of the invention in which the device 20 is employed in a coating operation wherein a photocured film or coating 21 is placed upon an object or substrate 22. The object or substrate 22 can be any object or substrate such as a floor, wall, table, windows or may be a moving substrate such as a plastic film or textile web. The surface 23 of the substrate may be curved or flat although it is preferred that the substrate is flat. In this embodiment, it is preferred that the light source 24 is an ultraviolet or blue light source, and that the photopolymer comprises a photocurable coating and that the thermometer comprises two or more noncontact temperature sensors 25 and 26. The light source may be moved or translated over the photocurable coating, or alternatively the light source is fixed and the coating moved, dependent upon which is more convenient or practical. It is preferred that the thermometer is a noncontact temperature sensor to avoid scratch or mar. It is preferred that the temperature is recorded at least once per second and more preferably at least ten times per second.

For exothermic polymerization reactions, the maximum rate of the temperature increase, i.e., the maximum slope (° C./sec.), corresponds approximately to the maximum rate of polymerization. As polymerization slows, the photocurable object is beginning to reach its "cured state", and the slope decreases and then finally goes negative (because the object is cooling, governed by Newton's law of cooling). A negative slope is indicative that the polymerization is complete or near complete, and that the light source may be turned off. Alternatively, a ratio of slopes may be used to approximate the cure state. For example, the light source may be turned off at a time when the slope is one-tenth the maximum slope recorded in the process.

It should be understood that these simple algorithms for determining cure state can be optimized and tuned via calibration of the process. One skilled in the art may calibrate the process by simply confirming the degree of polymerization (conversion of double bonds) or by testing the hardness of the object, or by other means. A microprocessor 27 is used to communicate the state of cure between the light source and the thermal detector.

One of the factors that may complicate the measurement is that the object may increase in temperature due to local heating from the light source. If this is the case, it is preferable to include a reference thermal detector, especially a thermometer. A reference thermometer is positioned such that it "sees" the light source but is not contained within, or focused upon, the photocurable object. In this manner two or more temperature recordings are taken and the reference temperature is subtracted in real-time, via the microprocessor, from the object temperature. This computed value is the temperature change due to polymerization only, and is a more accurate measure of the degree of polymerization. One skilled on the art may then tune and optimize the microprocessor to compute and indicate the most accurate degree of polymerization.

The temperature sensors may be placed in a variety positions or configurations, and one skilled in the art may determine through experimentation the configurations that are most appropriate. It is preferred that at least one non-contact temperature sensor is focused on the photocurable coating before it sees the light source and that at least one noncontact temperature sensor is focused on the photocurable coating after it sees the light source. In this manner the microprocessor can be set to compare the temperatures before and after exposure. The maximum rate of curing corresponds approximately to the maximum temperature difference between the temperature measured pre and post exposure. In this manner the microprocessor can be programmed to speed up or slow down the process instantaneously, to achieve maximum efficiency of the process.

It is preferred that at least at least two noncontact temperature sensors are employed, however, dependent upon the size of the operation it may be necessary to use ten or more sensors. The actual choice of sensors is dependent upon many factors including the distance of the sensor from the coating, the field of view of the sensor and the resulting "spot size" or focus spot of the sensor. The spot size or focus size is the diameter of the detectable area of the sensor. It is important that the sensor is focused such that it "sees" the photocurable object only and is not focused on adjacent or unrelated objects. This would cause error in the reading of the temperature. It is therefore preferred that the spot size is smaller than the photocurable object size, it is further preferred that the spot size is less than about 10 cm in diameter. Alternatively, it is possible to employ one or more thermal imaging cameras as the temperature sensor(s). In this manner, the recorded thermal videos can be used to thermally characterize the process and communicate information via a microprocessor to the coating system.

FIG. 2 shows the application of the invention in the field of dentistry. A noncontact temperature sensor 11 is placed at or near the distal end 12 of tip 13 of a dental curing lamp 10. The dental lamp tip is held in proximity of a composite tooth filling and the light source 15 is turned on to initiate polymerization. The noncontact temperature sensor records the temperature data throughout exposure and sends this information to a microprocessor 14 that via an algorithm, vide supra, determines the point at which curing is complete, and turns the light source 15 off. It is essential that the sensor is as small as possible since the distal-most end of lamp tip is typically about 1 cm in diameter and must be placed within the oral cavity. It is therefore preferred that the noncontact temperature sensor is a thermopile sensor 16 (FIG. 7B) which can be made as small as a few hundred microns. It is preferred that the microprocessor is housed within a body of the dental curing lamp to enhance its ergonomic design.

In the application of photocurable resin based composites in dentistry, the curing lamp is preferably a hand-held device 10. For curing purposes, it is typically held above the uncured composite at a distance (d), and for a time (s) that is arbitrarily selected by the operator and is believed to be sufficient to cure the composite (based upon the manufacturer's recommendations). However, there are many different types of dental lamps, with varied radiant spectrums and radiant power densities. The distance (d) is prone to operator error and the lamp tip or light exit position may be held within a few millimeters of the target, or its position may vary to as much as about 10 mm dependent upon the operator. This variation is significant since the radiant intensity of the curing light decreases with distance. The instant invention described herein may directly compensate, and correct for, many user variations since it provides a direct measure of the polymerization process.

In a specific embodiment, the invention provides a dental device comprising a dental curing light source having a wavelength capable of inducing polymerization of a photopolymer, and a noncontact thermometer capable of measuring the temperature or temperature change upon polymerization of the photopolymer, wherein the temperature change is used to indicate the approximate degree of polymerization. It is preferred that the dental curing lamp is a LED blue light lamp. It is preferred that the lamp has a collimated beam, or partially collimated beam. This is preferred because such lamps are safest for the operator and patient, and collimated beams have less radiant power loss with distance (d).

The preferred method for using the device for determining the cure state of a photocurable dental object comprises placing a photopolymerizable composite within an oral cavity, providing a dental curing device comprising a light source having a wavelength capable of inducing polymerization of the photopolymerizable composite, and a noncontact thermal detector, directing the light source to the photopolymerizable composite at a distance (d), wherein (d) is between 0 and 3 millimeters, turning on the dental curing device, collecting the temperature data with the thermal detector at a rate of at least 1 time per second, directing the collected data to the microprocessor, computing the slope of the temperature change with the microprocessor, selecting a slope value indicative of photopolymerizable composite cure, and turning off the light curing device when the slope value has been reached. An audio signal can be used to indicate that polymerization is complete, and the light source is powered off at the indicating signal.

In construction and use of the dental device of the invention, there are many requirements such as cost, size, ergonomic design and functionality.

Applications contemplated for the invention are not limited to the dental or medical industry as described in detail above. Light curable composites are used in a variety of industries, including paints & coatings, printing, including 3D printing, and in the composites industry (aerospace and medical composites). For all of these industries, effective and efficient curing is an important issue, and real-time information regarding the incident curing radiation may directly lead to manufacturing efficiency, product quality and cost improvement. A particularly important industry for application of the invention is the roll coating industry. In this industry, light curable resins are applied to a substrate that is moving, often rapidly at as much as several thousand feet per minute. The moving coating is then passed under curing lights to effect polymerization. The curing lights are typically extremely high powered UV lights that require extensive shielding and external cooling. Although the distance of the lamp (d) and exposure time (s) may be easily fixed by an engineer in such industrial systems, failed coatings due to insufficient cure are still the major cause of product failure. This is because the high energy lamps wear and their output decreases substantially over time. The invention described herein can be configured or optimized by one skilled in the art to create a device that monitors incident curing radiation in real-time.

EXAMPLES

Materials and Methods.

The curing lamp used for all examples was a Kerr DemiUltra LED with blue light emission centered at about 470 nm and a radiant power of 1100 mW/cm$^2$. The light exit position was the distal-most end of the tip.

Various thermal detectors were employed, including a k-type thermocouple detector model SC-TT-K-30-36-PP purchased from Omega engineering Inc. Noncontact thermopile detectors models MLX90615SSG-DAG, and MLX90614ESF-DCH were purchased from Melexis Inc.

Photopolymerizable dental composite, Sonicfil, A1 and A3 shades were obtained from Kerr Dental. The photopolymerizable composite was handled at all times under yellow lighting to prevent premature photopolymerization.

Figure 3:
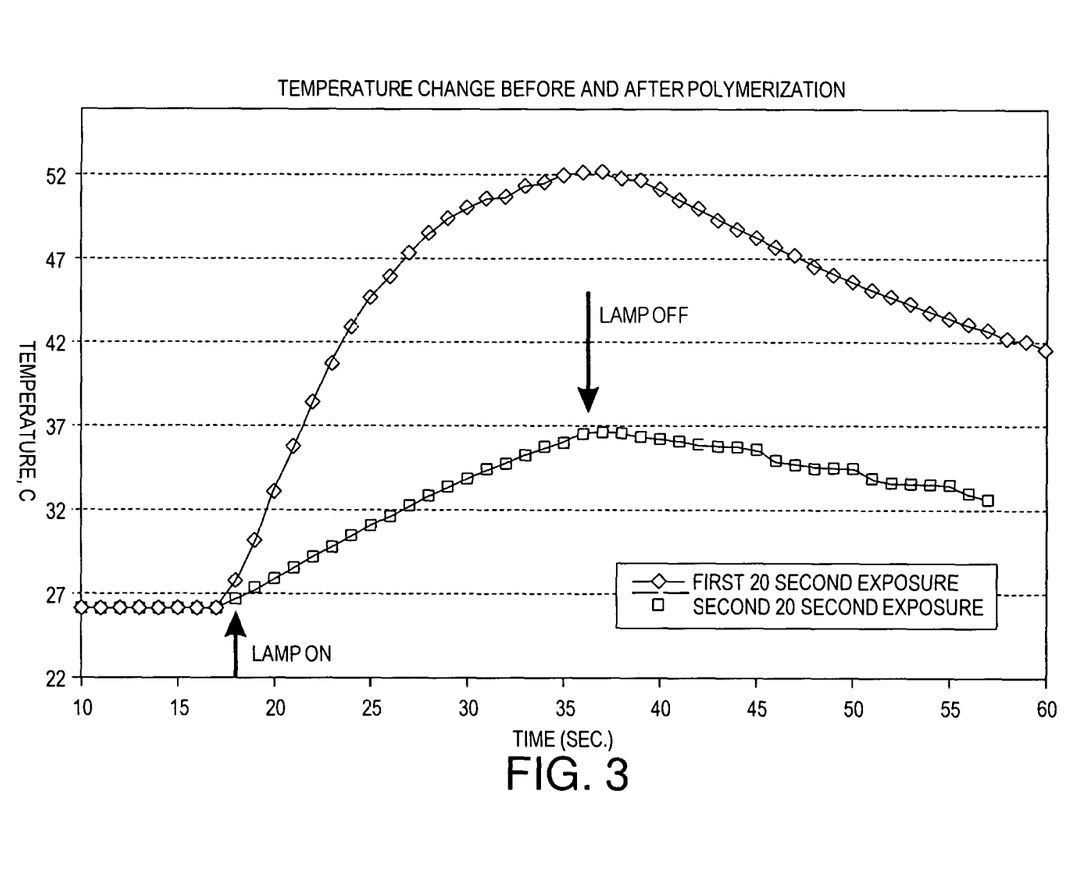
FIG. 3 shows the temperature versus time for a cylindrical composite specimen (9.9×3.4 mm) exposed 20 seconds with a dental curing lamp. The arrows indicate approximately where the dental lamp was turned on and off, respectively. See Example 1.

Example 1. Temperature Change as a Result of Photopolymerization of a Dental Composite Sonicfil dental composite, A3 Shade, was carefully packed into a nylon washer to create a cylindrical composite specimen; the diameter and thickness were 9.9 mm×3.9 mm, respectively. A small k-type thermocouple (wire diameter about 0.1 mm) was mounted in the center of the specimen so that its temperature could be recorded at one second intervals. The sample was exposed for 20 seconds using a fully charged, Kerr Demi Ultra dental lamp at a distance of 3 mm (lamp tip to the composite). After exposure the sample was allowed to cool to room temperature, and the hardness measured using a Shore D durometer; measurements greater than 90 indicated that the sample had been fully cured both front and back. The sample was then exposed with the dental curing lamp again under identical conditions, the temperature data were recorded again and the two, temperature versus time profiles, are shown in FIG. 3. The data indicate that a large, nonlinear temperature increase is observed during polymerization (first exposure) and that a smaller, and linear temperature increase is observed after polymerization is complete (second exposure). The latter temperature change is due only to heating from the lamp, whereas the former is due to the heat generated during polymerization and the heating from the lamp. The data demonstrate that a significant thermal signal is observed and is associated with polymerization of the photocomposite.

Example 2

Example 2 was performed identically to Example 1 above except that the specimen thickness was 1.9 mm.

Example 3

Example 3 was performed identically to Example 1 above except that the specimen thickness was 3.9 mm.

Example 4

Example 4 was performed identically to Example 1 above except that the specimen thickness was 5.0 mm.

Figure 4:
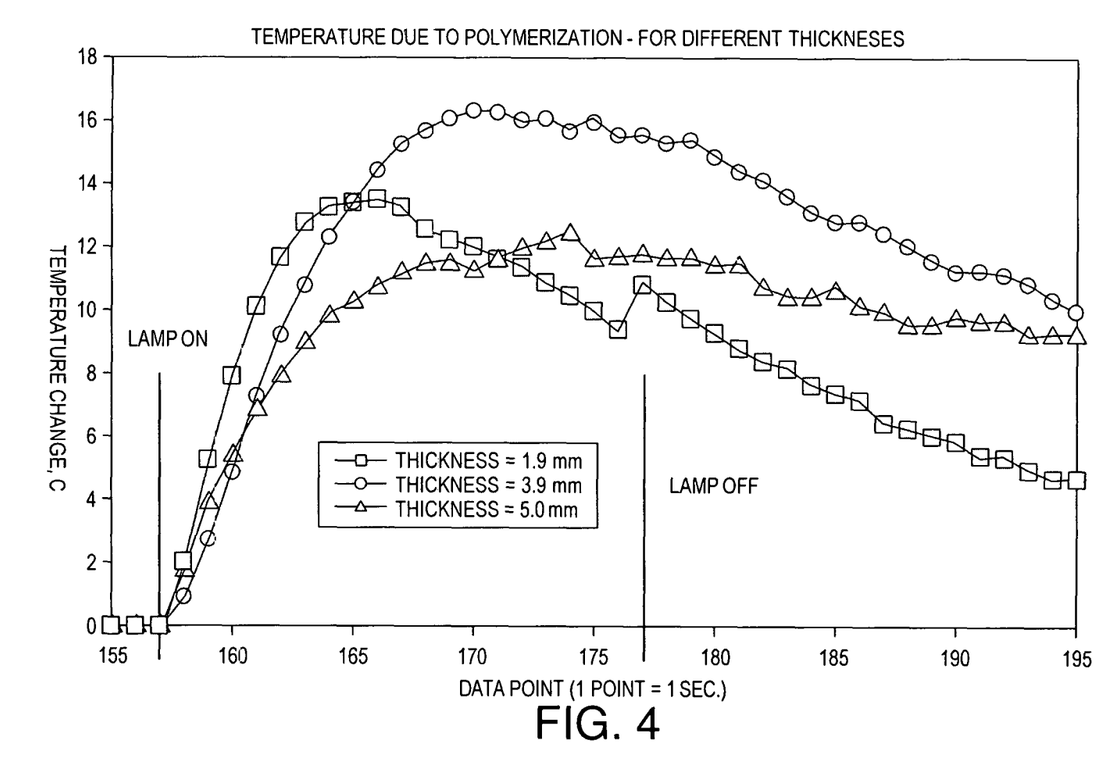
FIG. 4 shows the recorded temperature change versus light source exposure time for three composite specimens (examples 2-4), all having a diameter of 9.9 mm and thicknesses of 1.9, 3.9 and 5.0 mm, respectively. The vertical lines indicate the time at which the lamp was turned on and off, respectively.

FIG. 4 shows the temperature change versus light source exposure time for three composite pastes (Examples 2-4), all having a diameter of 9.9 mm and thicknesses of 1.9, 3.9 and 5.0 mm, respectively. The recorded temperature change due to lamp heating is subtracted from the curves so that the curves represent the temperature change due to the heat of polymerization only, and the data are normalized. The data indicate that polymerization occurs rapidly immediately after the curing lamp is turned on. The polymerization time can be roughly estimated from the peak temperature of the curves and is approximately 6, 13 and 18 seconds for the 1.9, 3.9 and 5.0 mm thick composites, respectively.

Example 5

Sonicfil dental composite, A3 Shade, was carefully packed into a nylon washer to create a cylindrical composite specimen; diameter and thickness were 9.9 mm×1.9 mm, respectively. The sample was exposed for 20 seconds using a fully charged, Kerr Demi Ultra dental lamp at a distance of 3 mm (lamp tip to the composite). During exposure, the temperature was recorded at intervals of 0.2 seconds using a Melexis 90615 noncontact temperature sensor, model MLX90615SSG-DAG, which was mounted 2.0 mm from the backside of the composite (opposite the lamp tip). After exposure the sample was allowed to cool to room temperature, and the hardness measured using a Shore D durometer; measurements greater than 90 indicated that the sample had been fully cured both front and back. The sample was then exposed with the dental curing lamp again under identical conditions, the temperature data were recorded again using the Melexis 90615. The temperature versus time profile for the second exposure was subtracted from that of the first exposure, so that only the temperature change due to polymerization was obtained. The data are plotted in FIG. 5.

Example 6

Example 6 was prepared and performed identically to Example 5, except that the specimen thickness was 3.4 mm Shore D durometer measurements were taken, giving averages values >90 indicating that the sample had been fully cured both front and back. The data are plotted in FIG. 5.

Example 7

Example 7 was prepared and performed identically to Example 5, except that the specimen thickness was 3.9 mm Shore D durometer measurements were taken, giving averages values >90 indicating that the sample had been fully cured both front and back. The data are plotted in FIG. 5.

Example 8

Example 8 was prepared and performed identically to Example 5, except that the specimen thickness was 5.0 mm Shore D durometer measurements were taken, giving averages values >90 for the front of the specimen (closest to the lamp tip); but gave an average value of 76 indicating that the backside of the specimen was partially cured. The data are plotted in FIG. 5.

Figure 5:
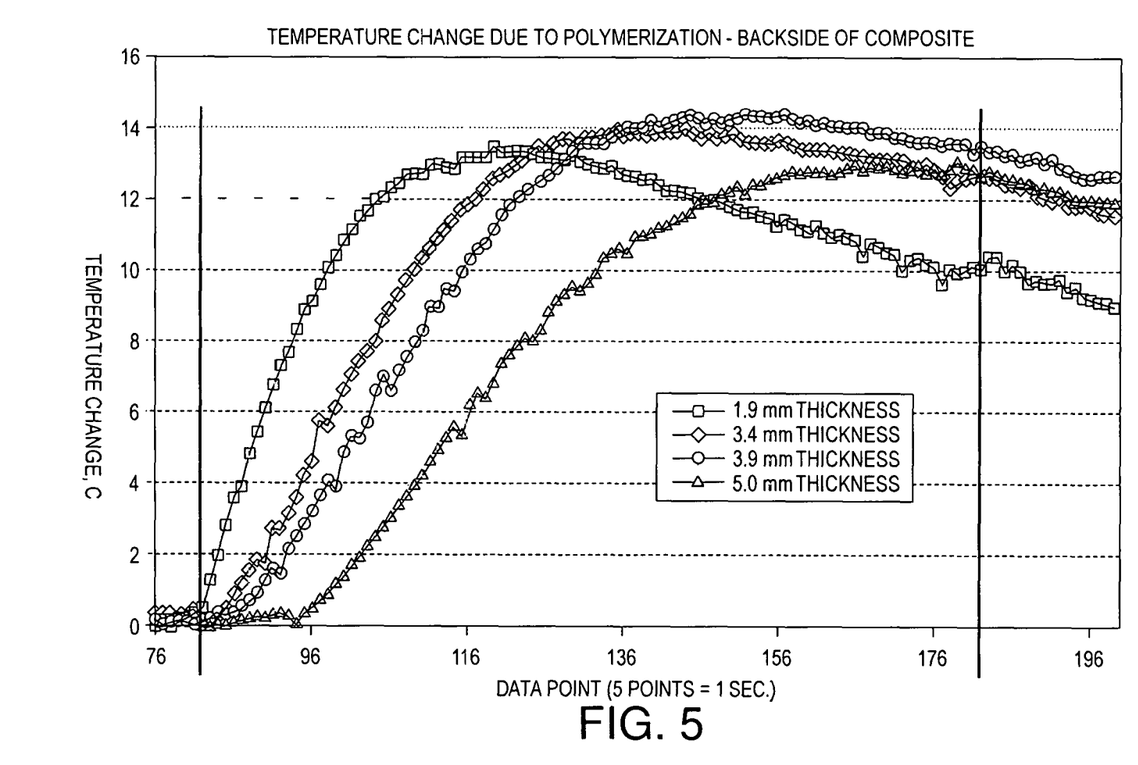
FIG. 5 shows the temperature change versus light source exposure time for composite specimens (examples 5-8), all having a diameter of 9.9 mm and thicknesses of 1.9, 3.4, 3.9 and 5.0 mm, respectively. The vertical lines indicate the points at which the curing lamp was turned on and off, respectively.

FIG. 5 shows the temperature change versus light source exposure time for composite specimens (examples 5-8), all having a diameter of 9.9 mm and thicknesses of 1.9, 3.4, 3.9 and 5.0 mm, respectively. The recorded temperature change due to lamp heating (second exposure) is subtracted from the curves so that the curves represent the temperature change due to the heat of polymerization only, and the data are normalized. The vertical lines indicate the points at which the curing lamp was turned on and off, respectively. The data indicate that polymerization occurs rapidly immediately after the curing lamp is turned on. The polymerization time can be roughly estimated from the peak temperature of the curves and is approximately 7, 11, 14 and greater than 20 seconds for the 1.9, 3.4, 3.9 and 5.0 mm thick composites, respectively. The data of FIGS. 5 and 6, taken together, indicate that temperature change is a useful and simple method to estimate the curing time of a photopolymerizable resin or composite. The use of a noncontact temperature sensor is especially useful since it does not require contact with the specimen during curing.

Example 9

Sonicfil dental composite, A3 Shade, was carefully packed into a nylon washer to create a cylindrical composite specimen; diameter and thickness were 9.9 mm×1.75 mm, respectively. The sample was exposed for 20 seconds using a fully charged, Kerr Demi Ultra dental lamp at a distance of 7 mm (lamp tip to the composite). During exposure, the temperature was recorded at intervals of 0.2 seconds using a Melexis 90615 noncontact temperature sensor, model MLX90614ESF-DCH, that was mounted at the tip of the curing lamp about 7.0 mm from the specimen. The field of view of the temperature sensor was 12 degrees so that the sensor measured the instantaneous temperature of the specimen over a spot size of about 1.5 mm After exposure, the sample was allowed to cool to room temperature, and the hardness measured using a Shore D durometer; measurements greater than 90 indicated that the sample had been fully cured both front and back. The data are plotted in FIG. 6.

Example 10

Example 10 was prepared and performed identically to Example 9, except that the specimen thickness was 2.1 mm After exposure of 20 seconds to the dental curing lamp, Shore D durometer measurements were taken, giving averages values >90, indicating that the sample had been fully cured both front and back. The data are plotted in FIG. 6.

Example 11

Example 11 was prepared and performed identically to Example 9, except that the specimen thickness was 3.43 mm After exposure of 20 seconds to the dental curing lamp, Shore D durometer measurements were taken, giving averages values >90, indicating that the sample had been fully cured both front and back. The data are plotted in FIG. 6.

Example 12

Example 12 was prepared and performed identically to Example 10, except that the specimen thickness was 4.3 mm After exposure of 20 seconds to the dental curing lamp, Shore D durometer measurements were taken, giving averages values >90, indicating that the sample had been fully cured both front and back. The data are plotted in FIG. 6.

Example 13

Example 13 was prepared and performed identically to Example 9, except that the specimen thickness was 5.7 mm Shore D durometer measurements were taken, giving averages values >90 for the front of the specimen (closest to the lamp tip); but gave an average value of 54 indicating that the backside of the specimen was very poorly cured. The data are plotted in FIG. 6.

Analysis of Data Obtained in Examples 9-13 (FIG. 6) and Prediction of Cure Time Using the Change in Slope of the Curves Obtained.

Figure 6:
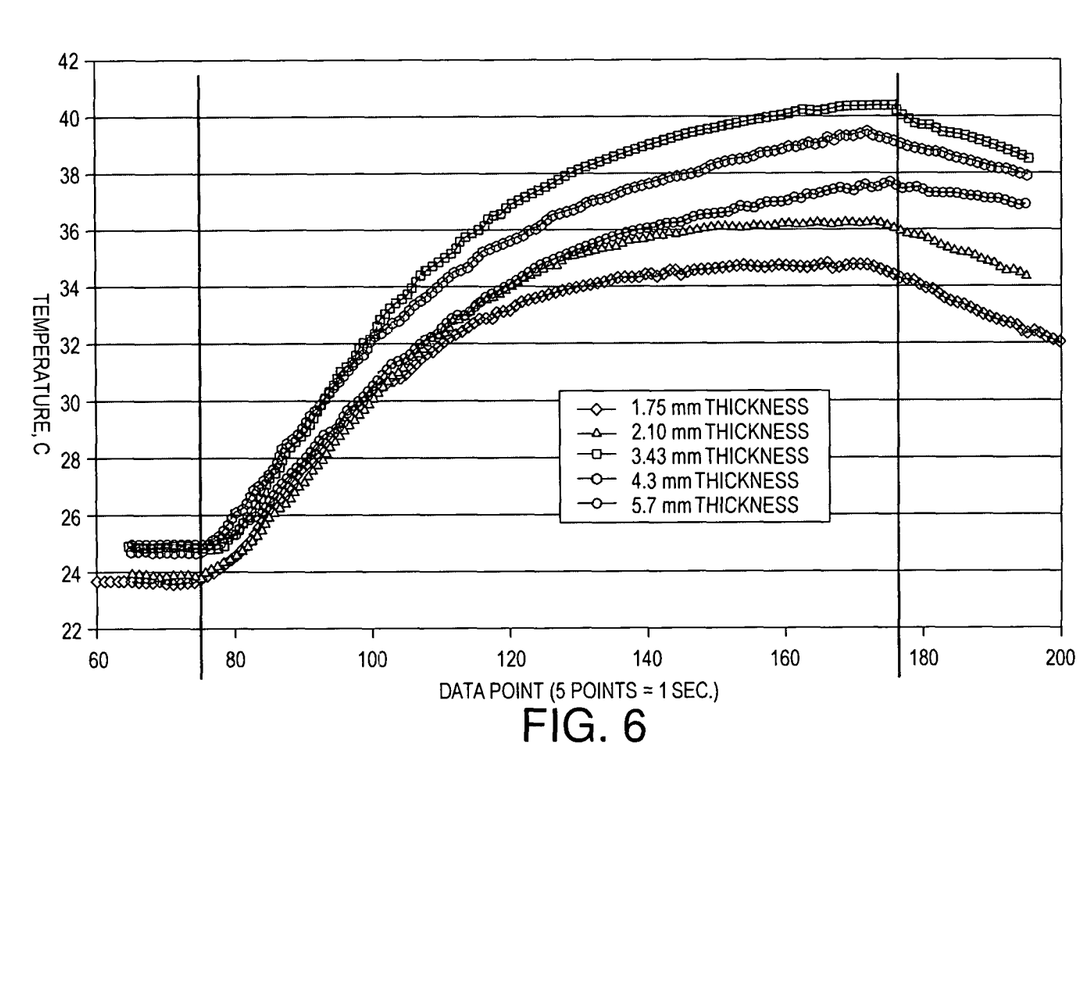
FIG. 6 shows the temperature versus time for cylindrical composite specimens (examples 9-13), all having a diameter of 9.9 mm and thicknesses of 1.75, 2.10, 3.43, 4.3 and 5.7 mm, respectively. The vertical lines indicate the points at which the curing lamp was turned on and off, respectively.

The following theory is presented to explain the curves obtained in FIGS. 5 and 6. It is known that the photoinitiated, free radical polymerization of light curable resins is an exothermic process, and therefore generates heat. Polymerization is initiated almost instantaneously upon irradiance with the curing lamp, however, because dental composites are opaque or translucent, and highly scattering to the incident curing radiation, the intensity of the curing radiation decreases with increasing thickness of the composite. Therefore, when measuring the temperature increase at the backside (opposite side of the curing lamp, FIG. 5) of the composite, there is a time delay in the temperature increase that increases with increasing thickness. Thus the polymerization reaction occurs as if a wave that moves through the composite from front to back. Polymerization proceeds rapidly at the front of this wave, but quickly slows as the monomers are polymerized and their concentration decreases, i.e., as the reaction moves toward completion. Once complete, heat is no longer generated and the object begins to cool as described by Newton's law of cooling. Therefore, the maximum polymerization rate of the composite is approximated by the maximum rate of temperature increase during exposure, and can be estimated by calculating a running slope in the temperature versus time curve. Further, the time to completion of the polymerization reaction can be approximated by the time at which the slope becomes negative, i.e, cooling is occurring. This situation is more complex for thicker composites, due to the lag in the polymerization reaction as a function of thickness, however, since their volume is greater, thicker composites take longer to cool and time to completion of the reaction can again be estimated by the change in slope, or the ratio of slopes taken at any two arbitrary points. The slope data for examples 9-13 are given in Table 1. A "running slope" was calculated over a time interval of 1 second (5 data points), using data collected at 0.2 second intervals.

TABLE 1

Slope data for Examples 9-13.

| | Example | | | | |
|---|---|---|---|---|---|
| | 9 | 10 | 11 | 12 | 13 |
| Specimen thickness (mm) | 1.75 | 2.1 | 3.43 | 4.3 | 5.7 |
| Maximum slope (° C./sec) | 1.9 | 1.6 | 2.1 | 1.8 | 1.5 |
| Time to maximum slope (sec.) | 2.2 | 2.2 | 2.4 | 2.6 | 3.6 |
| Time to reach $1/10^{th}$ maximum slope (sec.) | 11.8 | 14.0 | 15.8 | 17.8 | 20.0 |
| Time to reach a slope of zero (sec.) | 14.4 | 15.4 | 19.4 | 19.6 | 20+ |

The data of Table 1 indicate that the running slope at any time (t) can be used to give information about the cure state of a photocomposite or photocurable coating. During exposure the maximum slope observed corresponds approximately to the maximum rate of polymerization. The time to achieve maximum slope increases with composite thickness since the curing radiation is highly attenuated by the composite. We estimate that only about 1% of the incident curing radiation reaches a depth of 4 mm. The exposure time for achieving adequate cure of a specimen can be estimated by the change in slope during exposure. For example, the time required for the running slope to decrease to $\frac{1}{10}^{th}$ its maximum value, or the time required to reach a negative vale (when the polymerization reaction is complete and only cooling is observed). One skilled in the art may calibrate the system using a device that may indicates if the cuing has been complete (such as a scratch or hardness tester).

The invention claimed is:

1. A dental curing device comprising
   a light source having a wavelength capable of inducing polymerization of a dental composite in an oral cavity,
   a noncontact thermal detector in alignment with said light source to a spot directly within a beam of the light source as it impinges upon the dental composite and capable of measuring an instantaneous temperature of the dental composite upon polymerization, and
   a microprocessor
       for computing a slope of temperature change verses time of the dental composite upon polymerization and
       for selecting a slope change of said slope of temperature change to indicate the degree of polymerization of the dental composite,
       wherein said slope change computed and selected by said microprocessor is used to recognize or predict completion of cure time of the dental composite in real-time.

2. The dental curing device of claim 1 wherein the dental curing device is a hand-held dental curing device.

3. The dental curing device of claim 1, wherein the light source and said noncontact thermal detector are contained in a distal end of a tip of the dental curing device.

4. The dental curing device of claim 3, wherein the tip of the dental curing device is attachable to a housing.

5. The dental curing device of claim 1 wherein the light source is a blue LED curing lamp.

6. The dental curing device of claim 1 wherein the light source is an ultraviolet, visible or electron beam light source.

7. The dental curing device of claim 1 wherein the noncontact thermal detector is a thermopile sensor.

8. The dental curing device of claim 7, wherein the thermopile sensor is located adjacent the light source.

9. The dental curing device of claim 7, wherein the thermopile sensor is shielded from the light source by means of a long pass filter having a cut-off wavelength greater than 1000 microns.

10. The dental curing device of claim 7, wherein the thermopile sensor has a Germanium or Silicon window and is focused to a spot size of less than 1 cm.

11. The dental curing device of claim 1 wherein the noncontact detector is a noncontact thermometer and is focused to a spot size of less than 3 mm.

12. The dental curing device of claim 1 wherein the noncontact thermal detector has a field of view of less than 90 degrees.

13. The dental curing device of claim 1 wherein the noncontact thermal detector has a field of view of less than 30 degrees.

14. The dental curing device of claim 1 wherein the noncontact thermal detector is an optical pyrometer, thermopile sensor or thermal imaging camera.

15. The dental curing device of claim 1 further comprising a feedback loop for communicating completion of polymerization.

16. The dental curing device of claim 1 wherein the change in slope of the temperature or temperature change versus light source exposure time is equal to or less than 10% of a maximum rate of change.

17. The dental curing device of claim 16 wherein the maximum rate of change greater than 1.5 degrees Celsius per second.

18. The dental curing device of claim 1, wherein the noncontact thermal detector in alignment with said light source to a spot directly within a beam of the light source as it impinges upon the dental composite is focused on the spot with a lens.

* * * * *